US00PP27253P3

(12) United States Plant Patent
Olesen et al.

(10) Patent No.: US PP27,253 P3
(45) Date of Patent: Oct. 11, 2016

(54) *CLEMATIS* PLANT NAMED 'EVIPO048'

(50) Latin Name: *Clematis viticella*
Varietal Denomination: Evipo048

(71) Applicants: Mogens Nyegaard Olesen, Fredensborg (DK); Raymond Evison, St. Sampsons (GB)

(72) Inventors: Mogens Nyegaard Olesen, Fredensborg (DK); Raymond Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 25 days.

(21) Appl. No.: 14/121,291

(22) Filed: Aug. 15, 2014

(65) Prior Publication Data

US 2016/0050834 P1 Feb. 18, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

"Perfection by Poulsen—*Clematis* Main Varieties 2013" (3 pgs total).*

* cited by examiner

*Primary Examiner* — Susan McCormick Ewoldt

(57) ABSTRACT

A new *Clematis* plant with a compact growth habit, profuse, mauve flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

1 Drawing Sheet

Botanical classification: Genus: *Clematis*. Species: *viticella*.

Variety denomination: 'Evipo048'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1999 and the resulting seeds were planted the following winter in a controlled environment in Guernsey, Channel Islands, United Kingdom. The new variety named 'Evipo048' originated as a single seedling from the stated cross.

The new *clematis* plant may be distinguished from its female seed parent and male pollen parent primarily by differences in flower color. The new *clematis* variety has a tepal colour which is mainly Violet Group 85A. The female seed parent has a tepal colour which is Purple Group 76A. The male pollen parent has a tepal colour which is Red-Purple Group 65B.

The objective of the hybridization of this *clematis* plant was to create a new and distinct variety for nursery culture with unique qualities such as:

1. Uniform and abundant mauve flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo048' was selected by Mogens N. Olesen and Raymond J. Evison in their *clematis* development program in the Channel Islands, United Kingdom in 2000. Asexual reproduction of 'Evipo048' by means of vegetative cuttings and traditional layering was first performed by Mogens N. Olesen and Raymond J. Evison in the nursery during the summer of 2000. This initial and subsequent asexual propagations have demonstrated that the characteristics of 'Evipo048' are true to type and are transmitted from one generation to the next.

BRIEF DESCRIPTION OF THE DRAWING

The accompanying color illustration show as true as is reasonably possible to obtain in color photographs of this type the typical characteristics of the buds, flowers, leaves, and stems, of 'Evipo048'. Specifically illustrated in the drawing are flowers at various stages of development, flower in parts, leaves, and stems. Plants in the photographs are 2 years of age.

DETAILED DESCRIPTION OF THE VARIETY

The following is a detailed description of 'Evipo048', as observed in its growth throughout the flowering period in open air culture in Yamhill County Oreg. Observed plants were cultivated for a period of 18 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo023' described and illustrated in U.S. Plant Pat. No. 15,166 issued Sep. 21, 2004 are compared to 'Evipo048'in Chart 1.

CHART 1

| | 'Evipo048' | 'Evipo023' |
|---|---|---|
| Flower diameter | 120 mm | 90-120 mm |
| Tepal upper surface upon opening | Violet Group 85A with a central bar Purple Group 75B | Violet-Blue 91A |
| Compound leaf length | 115 mm | 180 mm |

FLOWER AND FLOWER BUD

Blooming habit: Recurrent. The natural flowering period is generally from May to September.

Flower bud:
- *Size*.—Normally 25 mm in length. Bud diameter is 10 mm.
- *Bud form*.—Elliptic.
- *Bud color*.—Yellow-Green Group 145B and 145C.

Peduncle:
- *Surface texture*.—Smooth.
- *Length*.—On average 30 mm.
- *Width*.—2 mm.
- *Color*.—Yellow-Green Group 145B.
- *Strength*.—Moderately strong.

Receptacle:
- *Surface texture*.—Lightly pubescent.
- *Shape*.—Funnel.
- *Size*.—2 mm (h)×3 mm (w).
- *Color*.—Yellow-Green Group 145B.

Flower arrangement:
- *Location on vine*.—New growth.
- *Borne*.—Normally in clusters of 3 to 5 flowers per stem.
- *Aspect*.—Flowers are oriented upwards.

Flower bloom:
- *Size*.—On average, flowers are 120 mm in diameter and 20 mm in depth.
- *Profile*.—Open flowers flattened convex.
- *Fragrance*.—None.
- *Lasting quality*.—Flowers normally remain 5 days on the plant.

Tepals:
- *Tepal color*.—The upper surface is Violet Group 85A with a central bar Purple Group 75B. The lower surface is Purple Group 85A with a central bar Yellow-Green Group 145D.
- *Quantity*.—Normally 6 tepals.
- *Size*.—60 mm in length by 35 mm wide.
- *Shape*.—Individual tepal shape elliptic. The tepal apex is mucronate. The tepal base is acute.
- *Apex recurvature*.—Slightly curved.
- *Tepal cross section*.—Slightly reflexed.
- *Margins*.—Entire. Strong undulations of margin observed.
- *Persistence*.—Tepals drop off cleanly.
- *Tepal overlap*.—Partial.

Reproductive organs:
- *Arrangement*.—Open.
- *Pollen*.—None observed.
- *Anthers*.—Size: 6 mm in length. Color: Yellow Group 8D. Quantity: On average, 55.
- *Filaments*.—Color: White Group 155A. Length: 7 mm.
- *Pistils*.—Quantity: On average, 30.
- *Stigmas*.—Level, relative to the length of the filaments and the height of the anthers.
- *Styles*.—Color: Green-White Group 157A. Length: 8 mm.

PLANT

Plant form: Climbing.

Plant growth: Moderately vigorous.

Size: Seasons growth attains 1.5 meters in height. Average spread is 45 cm.

Hardiness: Trials to date show the variety hardy in USDA Zones 4-9.

Stems:
- *Color*.—Juvenile stems are Yellow-Green Group 145A with intonations of Greyed-Orange Group 166D. Mature stems are Greyed-Orange Group 166B.
- *Internodes*.—On average, 9 cm between nodes.
- *Length*.—Normally 30 cm from the base of the plant to the flowering portion of the stem.
- *Diameter*.—Normally 3 mm.
- *Texture*.—Mature stems are ribbed.

Plant foliage:
- *Leaf characteristics*.—Deciduous.
- *Arrangement*.—Trifoliate.
- *Leaf size*.—Compound leaves are normally 115 mm (l)×100 mm (w). Leaflets are normally 40 mm (l)×24 mm (w).
- *Abundance*.—On average 2 leaves per 10 cm of stem.
- *Leaf color*.—Juvenile upper Yellow-Green Group 145A. Juvenile lower Yellow-Green Group 145B. Mature upper Yellow-Green Group 146A. Mature lower Yellow-Green Group 146B.
- *Stipules*.—Absent.
- *Petioles*.—Size: Normally 45 mm in length by 1 mm diameter. Texture: Smooth. Color: Greyed-Orange Group 166A on upper surface and Yellow-Green Group 144A on lower surface.
- *Petiolule*.—Size: Normally 10 to 25 mm in length by 1 mm diameter. Texture: Smooth. Color: Greyed-Orange Group 166A on upper surface and Yellow-Green Group 144A on lower surface.
- *Leaflet shape*.—Generally elliptic. The base is acute. The apex is acute.
- *Margin*.—Entire.
- *Surface*.—The upper side is smooth. The lower side is smooth.
- *Thickness*.—Moderate.
- *Glossiness*.—Not glossy.

Disease resistance: Subject to any disease that normally attacks the species. However the variety is more tolerant to *clematis* wilt, *Phoma clematidina*, than some *clematis*.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo048', substantially as described and illustrated, due to its abundant mauve flowers with good keepability, attractive long lasting foliage and compact growth, year round flowering under glasshouse conditions, suitability for production from softwood cuttings in pots, durable flowers and foliage which make the variety suitable for distribution in the floral industry.

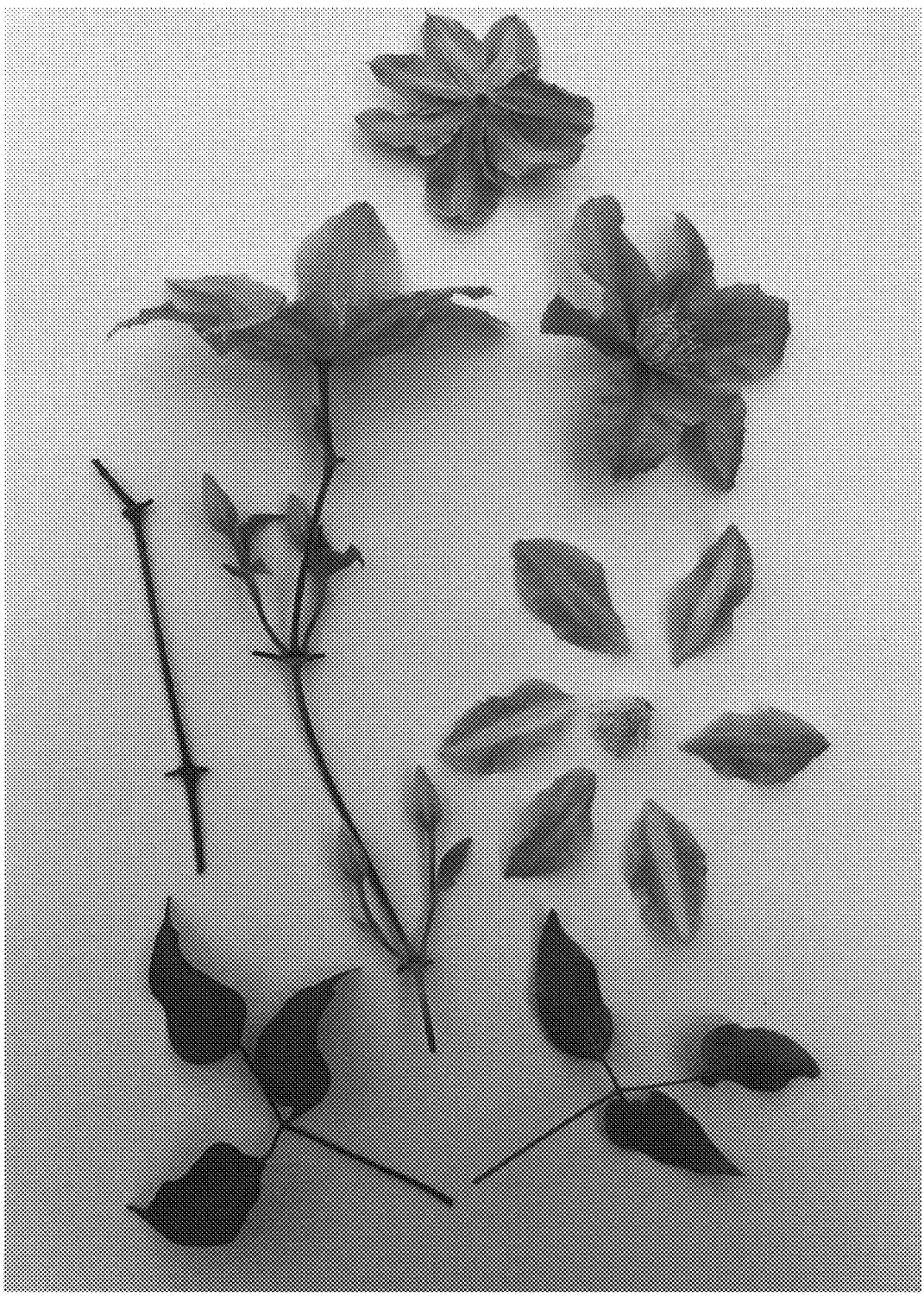

* * * * *